United States Patent [19]

Hotta et al.

[11] Patent Number: 4,500,459
[45] Date of Patent: Feb. 19, 1985

[54] TETRACYANOANTHRAQUINODIMETHANE COMPOUNDS

[75] Inventors: Shu Hotta, Hirakata; Tomiharu Hosaka, Yawata; Wataru Shimotsuma, Ibaragi, all of Japan

[73] Assignee: Matsushita Electric Industrial Co., Ltd., Osaka, Japan

[21] Appl. No.: 357,664

[22] Filed: Mar. 12, 1982

[30] Foreign Application Priority Data

Mar. 13, 1981 [JP] Japan ................................. 56-36728

[51] Int. Cl.³ ............................................. C07C 50/20
[52] U.S. Cl. ................................. 260/396 N; 252/500
[58] Field of Search ........................ 260/465 H, 396 N

[56] References Cited

U.S. PATENT DOCUMENTS 3,115,506 12/1963 Acker et al. ........................ 260/396
3,687,987 8/1972 Martin ............................ 260/396 N

OTHER PUBLICATIONS

Acker et al., J. Am. Chem. Soc., 84, 3370, (1962).
Wheland et al., J. Org. Chem., 40, 3101, (1975).
J. Chem. Phys. 70(05), Mar. 1, 1979, pp. 2215-2219, McIntyre et al.

Primary Examiner—Dolph H. Torrence
Attorney, Agent, or Firm—Wenderoth, Lind & Ponack

[57] ABSTRACT

A 11,11,12,12,-tetracyano-9,10-antraquinondimethane compound of the general formula

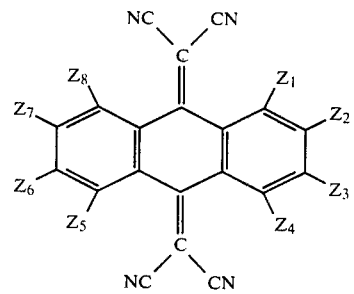

wherein $Z_2$, $Z_3$, $Z_6$ and $Z_7$ each is H, halogen, alkyl, phenyl, alkylphenyl, hydroxyalkyl, carboxyalkyl, hydroxy, amino or carboxy and $Z_1$, $Z_4$, $Z_5$ and $Z_8$ each is H, Cl, hydroxy or amino; said halogen being F, Cl, Br or I and said alkyl, alkylphenyl, hydroxyalkyl and carboxyalkyl each containing up to 8 carbon atoms.

The compounds within the scope of the above general formula are of value as organic conductors or organic semiconductors and can be used broadly as electronic materials.

1 Claim, 2 Drawing Figures

TETRACYANOANTHRAQUINODIMETHANE COMPOUNDS

BACKGROUND OF THE INVENTION

This invention relates to novel compounds, and more particularly to 11,11,12,12-tetracyano-9,10-anthraquinodimethane and its derivatives.

Heretofore, 7,7,8,8-tetracyanoquinodimethane (hereinafter referred to briefly as TCNQ) and 9,9,10,10-tetracyano-1,4-naphthaquinodimethane (briefly, TCNNQ) and various derivatives thereof (All of these compounds are collectively referred to as TCNQ and TCNNQ compounds) are known. These organic ompounds have excellent semiconductor characteristics and, as is well known, have great industrial values.

The molecular formulas of TCNQ and TCNNQ are presented hereinafter [(1) and (2), respectively]. TCNQ and TCNNQ, and various derivatives thereof have the tetracyanoquinodimethane skeleton represented by formula (3), and this skeletal structure is determinant of the characteristics of these compounds.

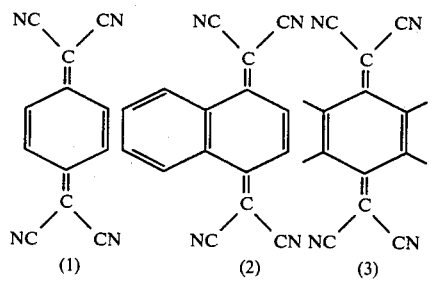

In this specification and the claims appended thereto, the term 'tetracyanoquinodimethane skeleton' means the skeletal structure consisting of those carbon and nitrogen atoms which constitute the molecule of TCNQ.

TCNQ and its derivatives have been described in the literature including D. S. Acker, et al., J. Am. Chem. Soc., 84, 3370 (1962) and R. C. Wheland, et al., J. Org. Chem.,40(21), 3101 (1975).

The structural analysis of TCNNQ has been attempted and reported in F. Iwasaki, Acta Cryst. B27, 1360 (1971).

SUMMARY OF THE INVENTION

This invention provides novel compounds which, based on the tetracyanoquinodimethane skeleton possessed in common, display certain characteristics which are not seen in TCNQ or TCNNQ or in any known derivative thereof.

The novel organic compounds according to this invention are 11,11,12,12-tetracyano-9,10,-anthraquinodimethane and its derivatives (hereinafter referred to as TCNAQ compounds), and may be represented by the following general formula (A).

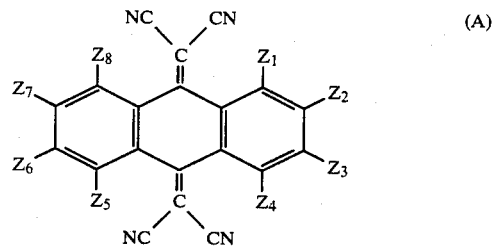

wherein $Z_1$ through $Z_8$ are as defined hereinafter.

A variety of TCNAQ compounds having useful characteristics can be obtained by selecting suitable species for substituents $Z_1$ to $Z_8$.

These derivatives can be easily produced from benzoquinone and butadiene derivatives.

DETAILED DESCRIPTION OF THE INVENTION

Figure 1:
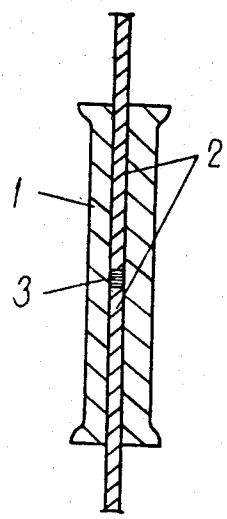
FIG. 1 is a longitudinal cross-sectional view showing a device for measuring electric resistances.

This invention will hereinafter be described in detail. As mentioned hereinbefore, the compounds according to this invention may be represented by the following general formula (A):

wherein $Z_1$, $Z_2$, ... $Z_8$ are substituent groups attached to $C_1$, $C_2$, ..., $C_8$, respectively, of 11, 11, 12, 12-tetracyano-9, 10-anthraquinodimethane (TCNAQ). More particularly, $Z_2$, $Z_3$, $Z_6$ and $Z_7$ each is H, halogen, alkyl, phenyl, alkylphenyl, hydroxyalkyl, carboxyalkyl, hydroxy, amino or carboxy; $Z_1$, $Z_4$, $Z_5$ and $Z_8$ each is H, Cl, hydroxy or amino.

The halogen referred to above may be fluorine, chlorine, bromine or iodine. The number of carbon atoms contained in said alkyl, alkylphenyl, hydroxyalkyl or carboxyalkyl may be 1 to 8.

The TCNAQ compounds (A) have a tetracyanoanthraquinodimethane skeleton in common and display excellent characteristics due to the electronic structure characteristic of the benzene rings located at both sides of the tetracyanoanthraquinodimethane skeleton. The term 'tetracyanoanthraquinodimethane skeleton' as used herein denotes the skeletal structure consisting of carbon and nitrogen atoms constituting the molecule of TCNAQ. Now, the characteristics of the tetracyanoanthraquinodimethane skeleton constituting the cardinal structure of the compounds of this invention will be explained and the TCNAQ compounds will be compared with TCNQ and TCNNQ compounds. The tetracyanoanthraquinodimethane skeleton has the following features.

(a) It has a tetracyanoquinodimethane nucleus;
(b) One or more substituents can be introduced into any one or more among $C_1, C_2, C_3, C_4, C_5, C_6, C_7$ and $C_8$.
(c) It has an aromatic benzene ring at both sides of its structure.

The semiconductor characteristics of TCNAQ compounds are derived from its tetracyanoquinodimethane structure (a). The other features (b) and (c) each provides basis for the versatility and functionality of the derivatives as organic compounds, and are the features which differentiate TCNAQ compounds from TCNQ and TCNNQ compounds.

Particularly, the tetracyanoanthraquinodimethane skeleton has a large expanse of electron cloud and due to the synergistic action of the tetracyanoquinodimethane nucleus and the benzene rings fused thereto at both sides, the energy breadth between the ground and excited states of electrons is so small that some useful results such as increased electrical conductivity are obtained. These features make TCNAQ compounds industrially useful organic compounds or organic semiconductors. Moreover, by varying the kinds and positions of substituents, varieties can be imparted to the above features. Taking their electrical characteristics as examples, the conductivity values of TCNAQ compounds (A) according to this invention lie in the range of about $10^{-9}$ to $10^{-7} \Omega^{-1}.cm^{-1}$.

Moreover, when, of the above-mentioned substituent groups, a chlorine atom, a hydroxy group or an amino group exists on $C_1$ of TCNAQ, there occurs a resonance (mesomeric effect) which extends the conjugated system of $\pi$ electrons on the tetracyanoanthraquinodimethane skeleton so that some useful results such as a remarkable increase of electrical conductivity are obtained. The above-mentioned resonance effect is schematically illustrated below.

obtained by using the compounds of this invention selectively in accordance with the intended use or application.

Some of such applications and uses will be described briefly.

(1.1) Polymers

Starting from TCNAQ compounds, various polymers having useful properties can be produced. The term "polymer" as used herein means a compound formed as a plurality of tetracyanoanthraquinodimethane skeletons are linked up either directly or through the intermediary of some other group or groups. The term "group" is used herein to mean an atom or a group of atoms.

By way of illustration, a polyether compound can be synthesized by condensing a TCNAQ derivative (A) having at least two hydroxyalkyl groups as substituents. Polyester compounds can also be synthesized by reacting a TCNAQ derivative (A) having at least 2 hydroxyalkyl groups as substituents with a TCNAQ derivative (A) having at least 2 carboxy or carboxyalkyl groups as substituents. Moreover, a halogenated derivative (A) can be dehalogenated by Ullmann reaction to obtain a polymer formed as a plurality of tetracyanoanthraquinodimethane skeletons are linked together.

(1.2) Charge transfer complexes

A TCNAQ derivative (A) or a polymer derived therefrom may be doped with a compound capable of acting as an electron donor or acceptor for it to obtain a charge transfer complex. Such electron transfer complexes have desirable characteristics and, therefore, are of great industrial value.

The above-mentioned TCNAQ compounds or polymers derived therefrom or charge transfer complexes based thereon may be dispersed or otherwise incorporated in other high molecular compounds or the like to provide compositions having very desirable properties.

As preferred examples of said electron donor, there may be mentioned such metal elements as sodium, copper, etc., aromatic compounds, e.g. anthracene, etc.,

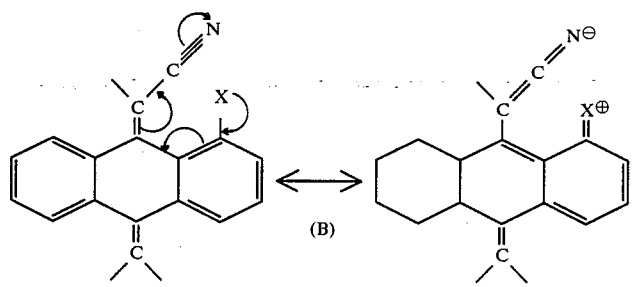

(1) Application and Uses

The TCNAQ compounds described above can be used in a variety of applications. Moreover, these compounds are useful as intermediates for the production of other valuable compounds or substances. Furthermore, these compounds or substances may be incorporated or dispersed in other inorganic compounds, organic compounds or high polymer compounds to provide compositions having desirable properties and characteristics. These compounds, substances and compositions generally can be used in a large variety of applications as organo-electronic materials. Desirable results can be amines and phthalocyanines. As for said electron acceptor, Lewis acids such as arsenic pentafluoride, etc. are especially desirable.

As matrices in which the compounds and derivatives according to this invention are incorporated or dispersed, various resins and other high molecular compounds are especially useful. In such applications, it is preferable to employ a compound (A) having substituents compatible with the high molecular matrix compound, for such a combination ensures a uniform composition or dispersion. For example, when a polyolefin compound is selected as said high molecular compound, an alkylated derivative (A) can be used with great advantage. When an aromatic high molecular compound is selected as the matrix material, it is advantageous to use a phenylated or alkyphenylated derivative (A).

These TCNAQ compounds and polymers and the charge transfer complexes derived therefrom, as well as compositions containing such compounds, polymers or complexes can be used in a large variety of applications as organoelectronic materials. For example, they can be used as dielectric materials, conductors, resistors, thermisters and other semiconductors, photovoltaic materials, and so on.

The method of producing TCNAQ compounds in accordance with this invention will hereinafter be described briefly, reference being made to TCNQ and TCNNQ compounds for comparison's sake. Thus, the methods of producing TCNQ compounds have been described in the literature such as D. S. Acker et al, J. Am. Chem. Soc. 84, 3370 (1962), R. C. Wheland et al, J. Org. Chem. 40 (21), 3101 (1975) and U.S. Pat. No. 3,115,506, for instance. By way of example TCNQ is produced from a diethyl succinate by converting the starting compound to 1,4-cyclohexanedione and reacting the latter with malonitrile. The process for synthesis of 1,4-cyclohexanedione from diethyl succinate has been described in J. R. Vincent et al, J. Org. Chem., 3, 603 (1939) and the subsequent process has been described in the above-mentioned paper of D. S. Acker et al.

One of the methods of producing TCNAQ compounds will be illustrated by way of chemical reaction formula [Formula (C)]. In Formula C, the substituents W, X, Y and Z are selected from among the substituents $Z_1$ through $Z_8$ in Formula (A).

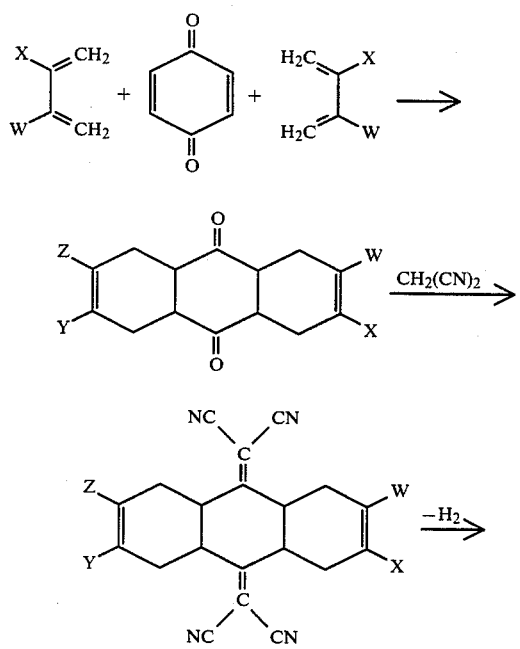

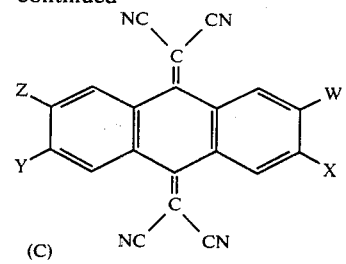

(C)

The following production examples are further illustrative of this invention.

The TCNAQ compounds (A) were produced in the following manner.

(i) Synthesis of 1,4,4a,5,8,8a,9a,10a-octahydro-9,10-anthraquinone derivatives 1,4,4a,5,8,8a,9a,10a-octahydro-9,10-anthraquinone compounds were produced from 0.5 mole of p-benzoquinone and 1.2 moles of butadiene or its derivatives.

The butadiene derivatives employed were 2-methylbutadiene, 2,3-dimethylbutadiene, 2-ethylbutadiene, 2,3-diethylbutadiene, 2-propylbutadiene, 2-butylbutadiene, 2-pentylbutadiene, 2-hexylbutadiene, 2-octylbutadiene, 2-phenylbutadiene and 2-(4-methylphenyl)-butadiene.

p-Benzoquinone and one of the above-mentioned butadiene derivatives were dissolved in benzene and the solution was refluxed at 70° C. Though varying somewhat with different species of butadiene derivative, the reaction yields were invariably in excess of 85 percent.

(ii) Synthesis of TCNAQ compounds 0.2 Mole of each 1,4,4a,5,8,8a,9a,10a-octahydro-9,10-anthraquinone derivative obtained in (i) and 0.24 mole of malonitrile were independently dissolved in 300 ml of benzene, followed by addition of 12 ml of acetic acid and 4 ml of ammonium acetate. The mixture was refluxed for 3 hours under constant stirring. The solution was then cooled and filtered and the crystals were recrystallized from acetonitrile to give the corresponding 1,4,4a,5,8,8a,9a,10a-octahydro-11,11,12,12-tetracyano-9,10-anthraquinodimethane derivative.

Of each of these compounds, a 0.1 mole portion was taken and, together with 0.12 mole of bromine, was added to 200 ml of acetonitrile cooled to 0° C. Then, in N₂ gas streams, 25 ml of pyridine was added and the solution was stirred at 0° C. for an hour. To the reaction mixture was added cold water and the resulting crystals were recovered by filtration and recrystallized from acetonitrile. The TCNAQ compounds produced in the above manner are shown in Table 1. Though varying somewhat with different species of TCNAQ compound, the yields were invariably over 90%. The overall yields of TCNAQ compounds through the above processes (i) and (ii) were invariably over 75%.

TABLE 1

| TCNAQ Compounds | | |
|---|---|---|
| Butadiene or its derivatives | | |
| W— | X— | TCNAQ Compounds |
| H— | CH₃— | 2,6-Dimethyl-TCNAQ, 2,7-Dimethyl-TCNAQ |
| CH₃ | CH₃— | 2,3,6,7-Tetramethyl-TCNAQ |

TABLE 1-continued
TCNAQ Compounds

| Butadiene or its derivatives | | |
|---|---|---|
| W— | X— | TCNAQ Compounds |
| H— | $C_2H_5$— | 2,6-Diethyl-TCNAQ, 2,7-Diethyl-TCNAQ |
| $C_2H_5$— | $C_2H_5$— | 2,3,6,7-Tetraethyl-TCNAQ |
| H | $CH_3(CH_2)_2$— | 2,6-Dipropyl-TCNAQ 2,7-Dipropyl-TCNAQ |
| H | $CH_3(CH_2)_3$— | 2,6-Dibutyl-TCNAQ, 2,7-Dibutyl-TCNAQ |
| H | $CH_3(CH_2)_4$— | 2,6-Dipentyl-TCNAQ, 2,7-Dipentyl-TCNAQ |
| H | $CH_3(CH_2)_5$— | 2,6-Dihexyl-TCNAQ 2,7-Dihexyl-TCNAQ |
| H | $BH_3(CH_2)_7$— | 2,6-Dioctyl-TCNAQ, 2.7-Dioctyl-TCNAQ |
| H |  | 2,6-Diphenyl-TCNAQ 2,7-Diphenyl-TCNAQ |
| H |  | 2,6-bis(p-Methylphenyl)-TCNAQ 2,7-bis(p-Methylphenyl)-TCNAQ |
| H | H | TCNAQ |

(Note)
W— and X— represent substituents in Formula (C).

In the above examples, when butadiene derivatives other than 2,3-dimethylbutadiene and 2,3-diethylbutadiene were used as starting materials, two stereoisomers were obtained for each derivative as shown in Table 1. In such cases, the reaction product was separated into the 2,6-di-substituted compound and 2,7-di-substituted compound by routine paper chromatography. Identification of the respective isomers was made by measurement of dipole moment, and the compound showing a dipole moment of o was identified to be the 2,6-di-substituted compound. Incidentally, the method of Wheland et al may be advantageously employed to obtain derivatives (A) having substituents in designated positions. This is because the inconstancy of addition reaction in the Diels-Alder system is then eliminated. Moreover, by using a mono-substituted anthracene, there can be obtained a mono-substituted TCNAQ. For example, TCNAQ mono-substituted by an alkyl, amino or other group can be obtained in this manner.

Figure 2:
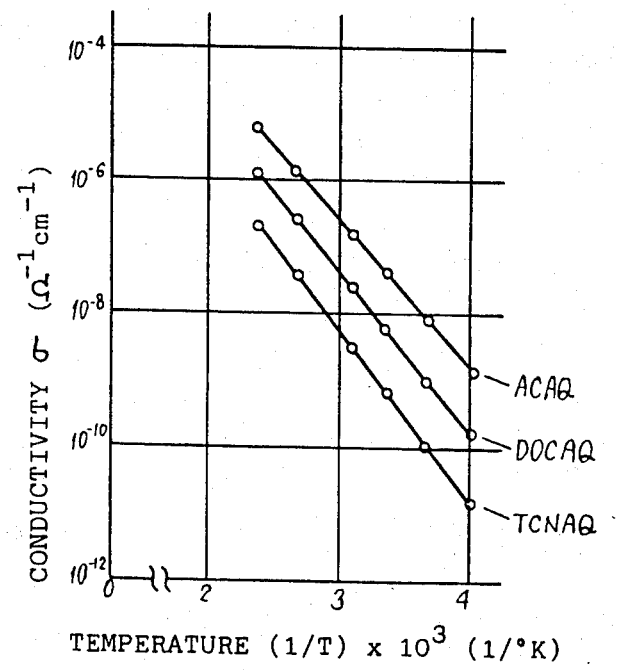
FIG. 2 is a diagrammatic representation of the conductivity-temperature characteristics (compressed powder samples) of 11,11,12,12-tetracyano-9,10-anthraquinodimethane (TCNAQ), 1,4-dihydroxy-11,11,12,12-tetracyano-9,10-anthraquinodimethane (DOCAQ) and 1-amino-11,11,12,12-tetracyano-9,10-anthraquinodimethane (ACAQ).

By the above procedure, it is easy to introduce a substituent onto one or more among $C_1$, $C_4$, $C_5$ and $C_8$. For example, DOCAQ and ACAQ, whose conductivity-temperature characteristics are shown in FIG. 2, were produced in this manner. In the investigation of those characteristics, the conductivity was measured by a device as shown in FIG. 1, where 1 denotes a glass capillary, 2 electrodes and 3 compressed powder sample.

What is claimed is:

1. A 11,11,12,12-tetracyano-9,10-anthraquinodimethane compound of the general formula

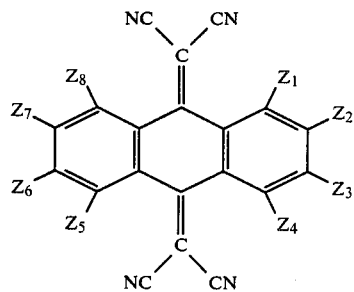

wherein $Z_2$, $Z_3$, $Z_6$ and $Z_7$ each is H, halogen, alkyl, phenyl, alkylphenyl, hydroxyalkyl, carboxyalkyl, hydroxy, amino or carboxy and $Z_1$, $Z_4$, $Z_5$ and $Z_8$ is H, Cl, hydroxy or amino; said halogen being F, Cl, Br or I and said alkyl, alkylphenyl, hydroxyalkyl and carboxyalkyl each containing up to 8 carbon atoms with the proviso that at least one of $Z_1$ to $Z_8$ must be halogen, hydroxy or amino.

* * * * *